United States Patent [19]
Acker

[11] Patent Number: 6,016,439
[45] Date of Patent: Jan. 18, 2000

[54] METHOD AND APPARATUS FOR SYNTHETIC VIEWPOINT IMAGING

[75] Inventor: David E. Acker, Setauket, N.Y.

[73] Assignee: Biosense, Inc., Setauket, N.Y.

[21] Appl. No.: 08/948,267

[22] Filed: Oct. 9, 1997

Related U.S. Application Data

[60] Provisional application No. 60/028,479, Oct. 15, 1996.

[51] Int. Cl.[7] ....................................... A61B 5/04
[52] U.S. Cl. ........................... 600/411; 600/414; 600/424
[58] Field of Search ..................................... 600/424, 410, 600/407; 128/920, 916; 382/128

[56] References Cited

U.S. PATENT DOCUMENTS

| | | |
|---|---|---|
| 4,638,798 | 1/1987 | Shelden et al. . |
| 5,230,623 | 7/1993 | Guthrie et al. . |
| 5,261,404 | 11/1993 | Mick et al. . |
| 5,291,889 | 3/1994 | Kenet et al. . |
| 5,329,310 | 7/1994 | Liljegren et al. . |
| 5,353,795 | 10/1994 | Souza et al. ........................ 128/653.2 |
| 5,378,915 | 1/1995 | Hines et al. . |
| 5,398,684 | 3/1995 | Hardy . |
| 5,417,210 | 5/1995 | Funda et al. ........................... 600/109 |
| 5,447,154 | 9/1995 | Cinquin et al. . |
| 5,483,961 | 1/1996 | Kelly et al. ........................ 606/130 X |
| 5,531,227 | 7/1996 | Schneider ............................... 600/107 |
| 5,548,694 | 8/1996 | Gibson ................................... 395/124 |
| 5,558,091 | 9/1996 | Acker et al. ......................... 128/653.1 |
| 5,594,842 | 1/1997 | Kaufman et al. ..................... 395/124 |
| 5,638,819 | 6/1997 | Manwaring et al. ................. 600/424 |
| 5,704,897 | 1/1998 | Truppe ................................... 600/117 |
| 5,752,513 | 5/1998 | Acker et al. ........................ 128/653.1 |
| 5,760,781 | 6/1998 | Kaufman et al. ..................... 345/424 |
| 5,776,050 | 7/1998 | Chen et al. ............................ 600/117 |
| 5,782,762 | 7/1998 | Vining ................................... 600/407 |
| 5,851,183 | 12/1998 | Bucholz ................................ 600/425 |

FOREIGN PATENT DOCUMENTS

| | | |
|---|---|---|
| WO 90/05494 | 5/1990 | WIPO . |
| WO 91/07726 | 5/1991 | WIPO . |
| WO 96/08209 | 3/1996 | WIPO . |
| WO 96/10949 | 4/1996 | WIPO . |
| WO 96/22048 | 7/1996 | WIPO . |

OTHER PUBLICATIONS

The Viewing Wand, Operators' Guide, ISG Technologies Inc., Jan. 1995.

M. Wapler et al., "Controlling Miniature Robotic Systems in Minimally Invasive Surgery" IEEE/RST/GI International Conference on Intelligent Robots and Systems, v. 1 (1994) pp. 711–716.

Barrie Sherman, "Virtual reality: a revenue generator for broadband?" Communications International, Dec. 1992, pp. 36–38.

A. Porter McLaurin, et al. "Virtual Endoscope," SPIE, vol. 2177, Jul. 1994, pp. 269–273.

William E. Lorensen, et al. "The Exploration of Cross–Sectional Data with a Virtual Endoscope," Interative Technology and the New Paradigm for Healthcare Chapter 36, 1995, pp. 221–230.

(List continued on next page.)

*Primary Examiner*—Francis J. Jaworski
*Attorney, Agent, or Firm*—Lerner, David, Littenberg, Krumholtz & Mentlik, LLP

[57] ABSTRACT

Medical apparatus for synthetic view point imaging includes an instrument insertable into the body of a patient. Using tissue image information defining an image of the patient's body, and defining the position of the distal end of the instrument within the body, synthetic images of the patient's body are synthesized having a viewpoint with a defined spatial relationship to the distal end of the instrument based on the image information and the determined position of the instrument.

50 Claims, 3 Drawing Sheets

OTHER PUBLICATIONS

John Morrissey, "Computers Put Surgical Sites in the Crosshairs," reprint from Modern Healthcare, Dec. 4, 1995.

Marvin P. Fried et al. "A New Armless Image Guidance System for Endoscopic Sinus Surgery," accepted from publication in Otoloryngology—Head & Neck Surgery, Oct. 16, 1995, pp. 1–4.

Roth et al., "Advantages and Disadvantages of Three–Dimensional Computed Tomography Intraoperative Localization for Functional Endoscopic Sinus Surgery," Laryngoscope, vol. 105, Dec. 1995, pp. 1279–1286.

Wada et al., "Three dimensional neuroimaging using computer graphics. Virtual endoscopy of the ventricular system," CI Kenkyu (Progress in Computed Imaging) (Japan) vol. 16:2 (1994) (Abstract only).

Wada et al., "Three dimensional neuroimaging using computer graphics. Virtual endoscopy of the ventricular system," CI Kenkyu (Progress in Computed imaging) (Japan) vol. 16:2 (1994) (Japanese article).

METHOD AND APPARATUS FOR SYNTHETIC VIEWPOINT IMAGING

CROSS-REFERENCE TO RELATED APPLICATIONS

The present application claims the benefit of United States Provisional Application No. 60/028,479, filed Oct. 15, 1996, the disclosure of which is hereby incorporated by reference herein.

FIELD OF THE INVENTION

The present invention relates to the field of endoscopy, and more particularly relates to methods and apparatus which provide synthetic images simulating those which would be seen from an instrument inserted into the body.

BACKGROUND OF THE INVENTION

Traditional medical endoscopes allow the physician to see structures inside the body and, in some cases, to treat the structures, as by performing a surgical procedure or applying a drug. Traditional endoscopes use a combination of lens systems and fiber-optic cable to convey images to an eyepiece or video monitor. Because the physician can observe the structures to be treated visually, from a viewpoint on the endoscope while performing the treatment, the physician gets an immediate, easy-to-understand picture of the spatial relationships between the endoscope, surgical tools inserted through the endoscope, and the surrounding bodily structures. If the endoscope moves to a new position in the patient's body, the lens moves with it and the physician's viewpoint also moves. The physician need not make mental computations to visualize the moved location of the endoscope, or to correct the image for the changed location. In this sense, the endoscope provides a natural viewing environment. For these reasons, endoscopic procedures have been adopted widely in many fields of medicine.

However, an endoscope must include an objective lens mounted adjacent the end advanced into the patient's body, referred to as the distal end of the endoscope, and must also include either an optical system such as a fiber optic or an electronic system such as a television camera and cable for relaying the images to outside of the patient's body. The endoscope must also include a light source or light conductor for illuminating the interior of the body. Although the art has devoted considerable time and effort to miniaturization of these components, typical endoscopes are still too large and inflexible to allow their insertion into many regions of the patient's body.

Moreover, the optical images from the endoscope contain information carried by light reflected from objects and surfaces in the forward viewing volume of the endoscopic lens, i.e., the volume seen through the lens. In most applications within the body, the forward viewing volume is bounded by an opaque surface such as the surface of an organ. Stated another way, the physician looking through an endoscope can only see what is visible through the lens; the physician cannot see what lies behind the surface of the organ. Also, the field of view and viewing direction are limited by the physical characteristics of the lens and other components. Thus, medical endoscopes are most commonly used to explore the inside of cavernous organs such as the alimentary tract or lungs.

Medical imaging procedures, such as magnetic resonance imaging (MRI) and computed tomographic (CT) imaging provide noninvasive visualization of the interior of a patient. Typically, however, MRI and CT imaging is performed pre-operatively for diagnostic purposes to provide the physician with images of the patient shown in various volumetric "slices."

Volumetric information or data obtained from CT, MRI and other similar medical imaging procedures has been recently used for "virtual reality" reconstruction to allow visualization of the imaging information in a three-dimensional environment. For example, in Sherman, "Virtual Reality; A Revenue Generator for Broadband?," Communications International (1992), a surgical simulator is described that can allow the surgeon to "fly around organs" to practice operations using remote controlled robotic instruments. The article describes that pictures are taken from a small remote-controlled video camera and superimposed on X-ray or MRI scans and viewed on a monitor. As with the use of an endoscope, however, this procedure apparently calls for the use of a small video camera, and therefore would suffer from the same limitations.

Wapler & Neugebauer, "Controlling Miniature Robotic Systems in Minimally Invasive Surgery", IEEE/RSJ/GI International Conference on Intelligent Robots and Systems, v.1 (1994), states that in a so-called virtual reality surgical environment, a surgeon can observe the current position of the endoscope tip relative to the patient in a computer-generated virtual image while also viewing the direct video images obtained by real video cameras in the endoscope itself. Thus, while viewing the real image obtained by the endoscope, the physician can see a video display showing an image reconstructed from MRI or CT data, with the endoscope superimposed on the image in a position corresponding to the position of the endoscope in the body. The viewpoint of the reconstructed image can be selected arbitrarily by the physician. PCT International Publication WO 96/08209 of Visualization Technology Inc. describes other systems which detect the positions of medical instruments and provide images of the patient's body with a representation of the instrument superimposed on the image. In certain embodiments using flexible instruments and magnetic position sensor at the time of the instrument, the '209 publication also employs a separate fiber optic endoscope inserted into the body along with the instrument to track movement of the instrument tip.

In McLaurin & Jones, Jr., "Virtual Endoscope," SPIE, Vol. 2177, an endoscope usable for medical and other applications requiring three-dimensional images is described. This article predicts that "there is a future potential for attaching the scope and camera devices to telepresent robots that can be guided in a number of ways."

Wada, et al., "Three dimensional neuroimaging using computer graphics. Virtual endoscopy of the ventricular system," C I Kenkyu (Progress in Computed Imaging) (Japan) v.16:2 (1994), describes virtual endoscopic imaging, i.e., a computer graphics system which generates an image simulating the image which would be seen from an arbitrary viewpoint specified by the user. Such imaging is described as useful for preoperative image training and simulation.

Lorensen et al., The Exploration of Cross-Sectional Data with a Virtual Endoscope, in Interactive Technology and the New Paradigm for Healthcare, Morgan et al., eds. (1995), describes a similar virtual endoscopic system which works with MRI or CT data defining a three-dimensional image of a patient. Using a mouse or other computer system input techniques, the user specifies an arbitrary position within the patient, and the system reconstructs an image which would be seen from an endoscope lens disposed at that position. By specifying a series of positions along a theoretical path, the user can effectively "fly through" the data, seeing a series of images which would be seen by an endoscope moving along the theoretical path.

Virtual reality techniques as taught in Wada et al. and Loernsen et al., however, do not allow the physician to treat the patient. Thus the physician can use these techniques to study a proposed operation beforehand, and to predict what will be seen during the actual operation, but cannot use these techniques to control the actual course of an operation or other interventional procedure.

PCT International Publication WO 91/07726 of I.S.G. Technologies, Inc., and an instruction manual entitled "The Viewing Wand" describe a device using a rigid instrument with an articulated arm mounted to the patient bed. The patient's head is clamped to the bed. Angular sensors in the articulated arm detect the disposition of the instrument, and a computer system transforms this disposition into registration with previously-acquired imaging data such as MRI data. The computer system reconstructs images of the patient, such as three-dimensional images of the body or selected parts or axial, coronal or saggital "slices", with pictures of the instrument superimposed thereon. Various computer graphics techniques can be used in the reconstruction. The three-dimensional images can be made translucent or partially translucent so that the instrument can be seen in the image. The computer system can also produce a two-dimensional "trajectory" image, taken on a plane perpendicular to the axis of the instrument, looking from outside the patient, and a "perpendicular" image, showing a two-dimensional view on a cutting plane perpendicular to the axis of the instrument, centered at the tip of the instrument. In an alternate arrangement shown in the '726 publication, the instrument may be provided with a large magnetic field sensor mounted at the proximal end of the instrument, on the handle thereof, and the position and orientation of the instrument may be determined by operating the sensor to detect magnetic fields sent from a transmitter mounted in fixed position relative to the patient.

Despite all of this effort, however, there have been needs for methods and apparatus which provide the intuitive visualization and treatment capabilities of a traditional endoscope without the size and other limitations of the traditional endoscope.

SUMMARY OF THE INVENTION

One aspect of the present invention provides apparatus incorporating a instrument, most preferably a flexible instrument, such as a catheter or other elongated element, having a distal end which can be inserted into the patient's body. Image storage means are provided for storing image information describing the patient's body, such as data obtained from magnetic resonance imaging or tomographic scanning of the patient. The apparatus also includes locating means for determining the position and preferably orientation of the instrument within the patient's body. Where the instrument is a flexible instrument, the locating means preferably is arranged to determine the position and orientation of the distal end of the instrument. Image generating means are provided for synthesizing synthetic images based on the position and, preferably, orientation of the instrument as well as the stored image information. The synthetic images have a viewpoint at a specified location on the instrument, preferably adjacent the distal end thereof. Stated another way, the synthetic image presented at any time corresponds to the image which would be seen by a theoretical endoscope having a lens at the specified location relative to the instrument. That is, the geometrical relationships among anatomical features in the synthetic image, and the geometrical relationship between the anatomical features and the instrument, is the same as it would be in an image provided by the theoretical endoscope. The viewpoint of the synthetic image thus has a defined spatial relationship to the instrument. This spatial relationship preferably remains fixed unless and until the user changes it. The synthetic image preferably is generated in real time, so that the viewpoint of the image moves as the instrument moves in substantially the same way as a real endoscopic image. However, the instrument need not incorporate the real physical elements, such as a lens, needed in a real endoscope. Accordingly, the instrument may be far smaller than a real endoscope. Further, any instrument having a part which is inserted in the body and which can be located during use can be employed. For example, where a surgical procedure employs several instruments inserted into the body, each instrument can be provided with a sensor so that the position and location of its distal end can be monitored. The system can provide plural synthetic images with different viewpoints associated with the plural instruments.

Moreover, preferred apparatus according to this aspect of the invention can provide imaging capabilities not attainable in a conventional endoscope. Because the image generation means constructs synthetic images from the stored image information, the characteristics of the image can be altered by changing the reconstruction parameters, preferably without changing any physical element of the instrument. Thus, the image generation means may include means for selecting desired characteristics of the synthetic images as specified by the user during the procedure. These characteristics may include the spatial relationship between the viewpoint and the instrument, such as specified location on the instrument where image is acquired (the location of the theoretical viewing lens), as well as the field of view or angle encompassed by the image and the viewing direction, i.e., the direction in which the theoretical lens points.

Preferably, the synthetic images are generated by "volume visualization" techniques, in which the image is generated based on tissue image data in a three-dimensional viewing volume such as a cone projecting outwardly from the viewpoint. The images may be generated on the basis of assumed optical properties of tissues, as well as assumed illumination from a theoretical light source. The assumed optical properties of each tissue, such as its reflectivity, opacity and color may match the real optical properties, or else may be selected to enhance visibility. For example, a tissue may be shown in one color and a lesion having magnetic resonance characteristics different from the tissue may be shown in a contrasting color even though the real lesion has a true color close to that of the tissue. Because the assumed opacity of the tissues can be selected at will, the physician can look through the walls of organs appearing in the field of view to gain a better understanding of the surrounding region. The preferred apparatus thus can combine the benefits of a real endoscope, with its readily understandable image, realistic movement as the instrument moves, and ability to perform an interventional procedure to treat the patient, with the ability to alter the view at will simply by altering user-selected parameters in a computer image reconstruction procedure. Similarly, characteristics of the assumed illumination, such as its assumed brightness and the location of the assumed illumination source, can be altered at will.

Preferably, the instrument has a sensor, such as a magnetic field detector or an antenna disposed adjacent the distal end, and the locating system is arranged to detect position and orientation of the sensor by transmitting one or more fields to or from the sensor and monitoring characteristics of the transmitted fields. Typically, the image data includes information such as magnetic resonance characteristics or X-ray absorption of the tissues in volume elements or "voxels", the voxels being arranged in a frame of reference referred to herein as the tissue image reference frame. The locating means typically acquires position and orientation of the sensor with respect to a second reference frame, referred to herein as a locating system reference frame. Preferably, the image generation means including means for registering the position and orientation of the instrument with the image information in a common reference frame, as by transforming the position and orientation as determined by the locating means into a position and orientation in the tissue image reference frame. The registration means preferably includes imaging fiducial markers attachable to the patient and imaged by the imaging procedure for establishing the tissue image reference frame, as well as a reference sensor attachable to the patient. As further discussed below, the fiducial markers can be used to determine a transformation between the reference frames, whereas position and orientation of the reference sensor can be monitored to determine changes in the transformation. The patient need not remain immobile during use of the instrument.

Further aspects of the present invention include methods of providing images during an interventional procedure corresponding to images which would be seen from a viewpoint on a instrument inserted within a patient. A method according to this aspect of the invention desirably includes the steps of (a) inserting a distal end of a instrument such as a flexible instrument into the patient's body; (b) providing image information of the patient's body relative to a reference frame; (c) determining the position of the distal end of the instrument; and (d) synthesizing synthetic images of the patient's body during the interventional procedure based on the image information and the determined position of said instrument. The synthetic images preferably have a viewpoint corresponding to a selected position on the instrument adjacent the distal end thereof. The method may further include the step of determining the orientation of the instrument within the patient's body, and the step of synthesizing may includes synthesizing said synthetic images based on the stored image information and determined position and orientation of the instrument.

According to one aspect of the invention, the step of locating includes transmitting signals from transmitting means and sensing the transmitted signals by sensing means associated with the instrument to determine the location of the instrument. Alternatively, the step of locating includes transmitting signals from transmitting means associated with the instrument and sensing the transmitted signals by sensing means to determine the location of the instrument.

Preferably, the step of synthesizing includes synthesizing the synthetic images in real-time during the interventional procedure and the method also includes the step of displaying the synthetic images on a display monitor. As discussed above in connection with the apparatus, characteristics of the synthetic images can be adjusted such as by selecting a desired view direction assumed optical properties of the tissues and assumed illumination parameters. As discussed above, transparency can be included in the assumed optical properties assigned to surrounding tissue so as to allow visualization of areas of tissue beyond the immediate vicinity of the instrument, and beyond optically opaque boundaries such as organ walls.

Methods according to this aspect of the present invention may include the step of treating the patient in the vicinity of the instrument distal end, as by inserting a tool or administering a medicament through the instrument. The step of providing the imaging information may be performed by magnetic resonance imaging using a conventional MRI magnet assembly and associated components. The interventional procedure, including the step of inserting the instrument may be performed while the patient is positioned in the MRI magnet assembly, and the step of determining the position and orientation of the instrument may include the step of operating a sensor on the instrument to monitor one or more magnetic fields generated by the MRI magnet assembly The foregoing and other objects, features and advantages of the present invention will be more readily apparent from the detailed description of the preferred embodiments set forth below, taken in conjunction with the accompanying drawings.

DETAILED DESCRIPTION OF PREFERRED EMBODIMENTS

Figure 2:
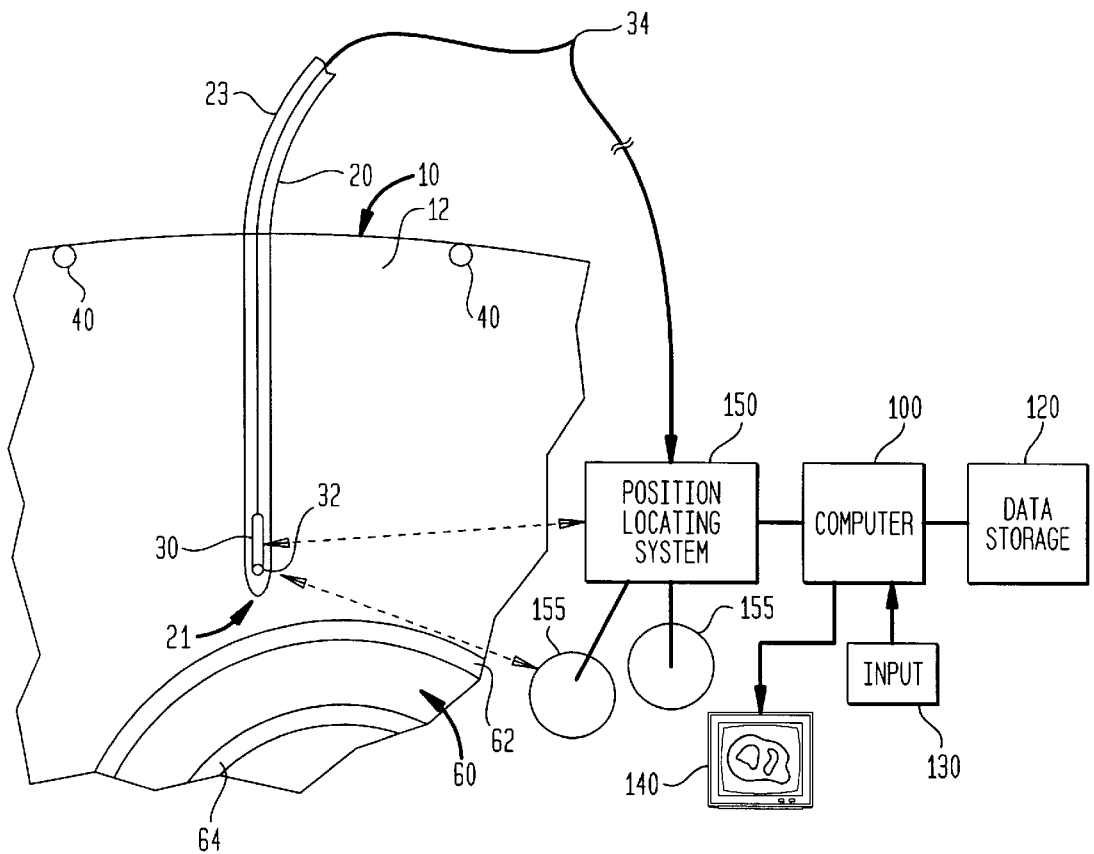
FIG. 2 is a fragmentary, diagrammatic view of apparatus in accordance with a preferred embodiment of the present invention.

A patient 10 is shown in a first or tissue image reference frame XYZ. Tissue image reference frame XYZ corresponds to the frame of reference that is used during a scanning procedure of the area of interest of patient 10. For example, the patient is subjected to a conventional imaging procedure such as magnetic resonance imaging or CT imaging. The scanned area of patient 10 can consist of any portion of the body of interest in which an interventional procedure is to be performed, such as the brain, chest, knee, etc. Referring to FIG. 2, patient 10 includes an interior portion 12 which contains tissue, bone, cartilage, fluid and other materials and objects, such as object 60, which could represent a lesion, tumor, organ, bone portion, etc. found within the human body.

Apparatus according to one embodiment of the invention includes an instrument 20 Preferably, instrument 20 is an elongated, flexible instrument such as a catheter or wire having a distal end 21 and a proximal end 23 (FIG. 2). A probe or sensor assembly 30 is mounted on instrument 20 at or adjacent to distal end 21. Probe 30 includes a sensor 32. Conductors 34 attached to the sensor extend lengthwise along instrument 20 towards proximal end 23 to convey the signal information received by the sensors to the position locating system. U.S. Pat. Nos. 5,480,422, 5,383,454, 5,295, 486 and 5,437,277 and 5,558,091, as well as PCT application PCT/US95/01103, describe a few of the many types of sensors which can be employed. The disclosures of these patents and application are incorporated herein by reference. The sensor or sensors desirably is a three-axis magnetic field sensor as disclosed in U.S. Pat. No. 5,558,091 or the corresponding International Patent Publication WO 95/09562, the disclosure of which is hereby also incorporated by reference herein. As described in the '562 publication and '091 patent, such a sensor may include three magnetoresistive or Hall-effect devices mounted with their sensitive axes orthogonal to one another, so as to provide separate signals representing the separate components of the magnetic fields in three orthogonal directions. Probe 30 need not incorporate an optical imaging system and therefore can be extremely small in size. Desirably, the probe, and hence the sensor or sensors included in the probe, has a diameter or dimension in the direction transverse to the direction of elongation of instrument 20 smaller than 5 mm, preferably smaller than 3 mm and most preferably about 1 mm or less. For example, the probe may have a length of about 3 mm and a diameter of about 1 mm. The diameter of instrument 20 may be as small as the diameter of the probe, or else may be larger so that instrument 20 can accommodate an interior lumen 25 extending from the proximal end to a port adjacent the distal end 21 of instrument 20. Other devices and features (not shown) which facilitate treatment of the patient at the distal end of the instrument may also be incorporated in the instrument. For example, the instrument may include remotely operable surgical tools disposed at the distal end.

The apparatus further includes a position locating system 150 adapted to determine the position and orientation of sensor assembly 32. The details of useful locating systems are known, and are fully described in the patents and publications incorporated by reference herein, and accordingly are only described in summary herein. The locating system may include a set of magnetic field transmitting coils 155 disposed adjacent a patient-receiving space, as well as actuating devices (not shown) for supplying currents to the coils so that the coils emit magnetic fields. The components of the magnetic fields generated by the coils vary in intensity with position in a locating system coordinate system X'Y'Z' (FIG. 1) according to a known pattern. Thus, by monitoring the magnitudes of the magnetic field components detected at sensor 32, and applying appropriate mathematical field equations, locating system 150 can determine the position and orientation of sensor 32, and thereby determine the position and orientation of the distal end 21 of instrument 20 in the locating system X'Y'Z' coordinate system. A reference sensor 43, substantially identical to sensor 32, is also provided. As further discussed below, reference sensor 43 is attached to the outside of the patient's body during use of the system, and is used to maintain registration between the location system and the tissue image data by correcting for patient movement. Reference sensor 43 is connected to locating system 150 in the same manner as sensor 32. The locating system can determine the position and orientation of reference sensor 43 in the same manner as discussed above with respect to sensor 32.

The apparatus also incorporates a digital data storage device 120 for storing image data, such as magnetic resonance imaging (MRI) or computerized tomographic imaging (CT) data defining an image of the patient. Typically, such image data includes digital information specifying a parameter such as magnetic resonance intensity or X-ray absorptivity for each of many volume elements (voxels) in the patient. Essentially any device capable of storing digital information, such as semiconductor memory, magnetic disk memory, optical disc memory and combinations of these, may be used as storage device 120. A computer 100 is linked to data storage device 120, and to position locating system 150. The computer preferably is a general-purpose digital computer programmed to perform the operations discussed below. Computers of the type commonly referred to as "workstations" can be employed. Conventional input devices 130 such as a keyboard and a mouse or other pointing device are also linked to the computer. A display device 140 such as a conventional monitor screen or flat panel display linked to the computer.

In this embodiment, fiducial markers 40 are provided. The fiducial markers are formed from materials which can be readily imaged. For example, if proton-based MRI imaging is employed to collect the imaging data, the fiducial markers may be formed from a material having high proton density and may have distinctive shapes, different from those of natural structures, so that the fiducial markers can be spotted readily in an MRI picture. If an X-ray based imaging modality such as CT imaging is employed, the fiducial markers may be formed from a metal or other X-ray opaque material.

Figure 1:
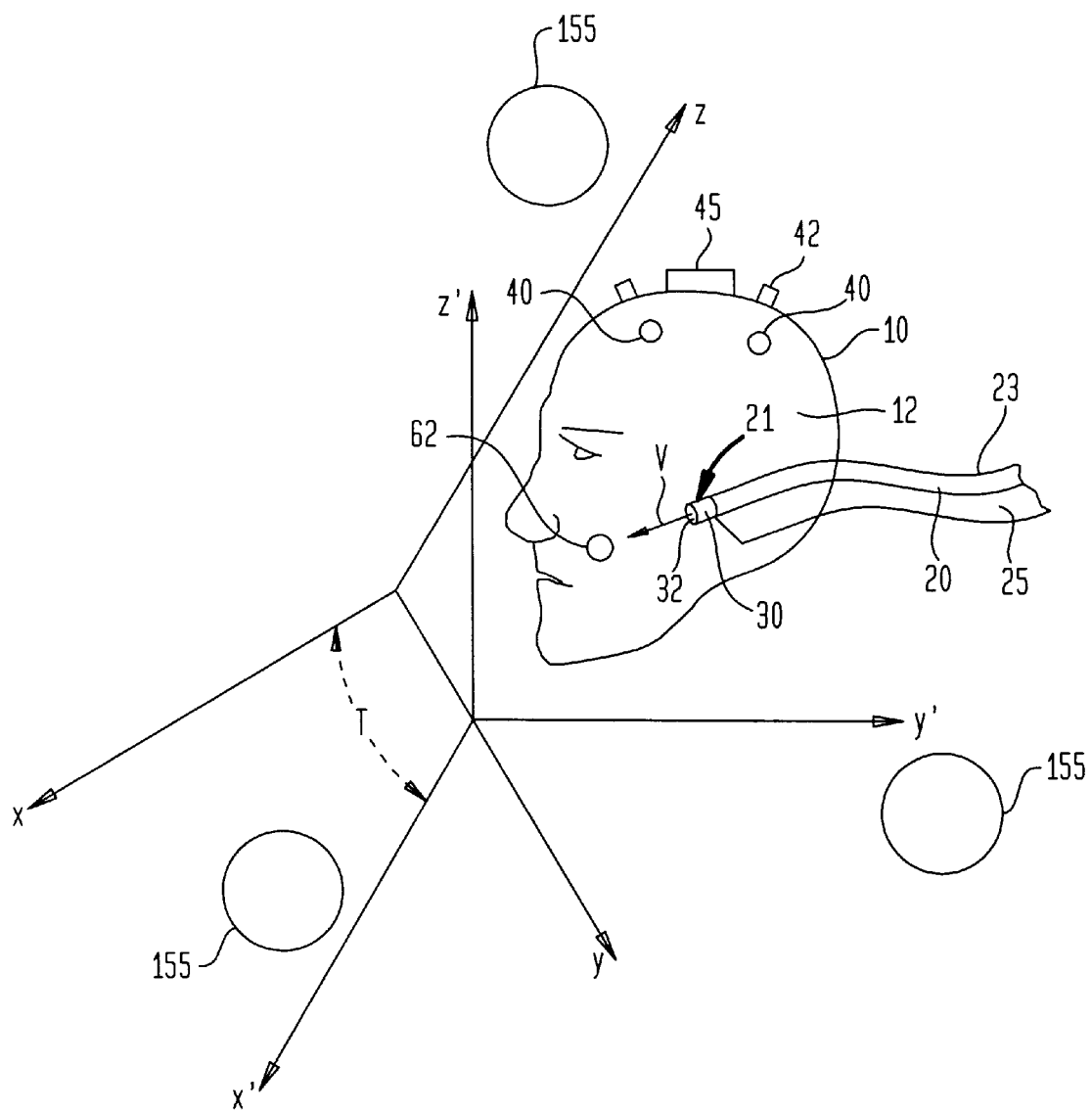
FIG. 1. is a diagrammatic, perspective view showing both the tissue image reference frame and the patient reference frame.

In a method according to one embodiment of the present invention, image information is first obtained of by subjecting a region of interest in the patient's anatomy, such as the head depicted in FIG. 1, to conventional MRI or CT scanning procedures. The scanning step may be performed in any scanning instrument, independently of the locating system discussed above. In the normal manner, the scanning procedure yields a set of image data. The image data is acquired in the frame of reference of the imaging instrument, denoted by coordinates X,Y,Z in FIG. 1. Fiducial markers 40 are mounted on the patient prior to the scanning step, and hence are incorporated in the image data derived by the scanning procedure. Desirably, fiducial markers 40 are mounted to rigid structures of the patients anatomy, such as to the skull or other bones. The fiducial markers may be disposed on the outside of the patient's body. Preferably, the fiducial markers are mounted in regions of the anatomy where there is only a small amount of soft tissue between the skin and the underlying bone. For example, fiducial markers can be mounted to the skin on the forehead, on the scalp or onto the bridge of the nose. Images of fiducial markers 40 will then appear in the image data for registration purposes.

After the scanning step, the image data is transferred from the imaging system to the storage unit 120. The patient is placed in proximity to the sensing system 150, including coils 155 in an environment suitable for the interventional procedure which will be performed. For example, the sensing system may be located in an operating room, and the patient may be located in the operating room. Registration sensor 43 is attached to the outside of the patients body, as by taping the registration sensor to the skin, in a location close to fiducial markers 40. The registration sensor desirably is disposed in a location where there is only a small amount of soft tissue between the underlying bone and the skin. The locations of the fiducial markers in the XYZ tissue image coordinate system are input to the computer. For example, an image of the patient reconstructed from the stored image information can be displayed on screen 140, and input devices 130 can be actuated to adjust the coordinates of a cursor in the tissue image coordinate system until the cursor is aligned with the depiction of a fiducial marker. The region of the patient bearing the fiducial markers and registration sensor, such as the patients head in FIG. 1, is immobilized temporarily. Instrument 20 is maneuvered to touch a first fiducial marker 40 with probe 30, and thereby bring sensor 32 into coincidence with that fiducial marker. At this time, input device 130 is actuated to send a signal to the computer confirming that the sensor is coincident with the first fiducial marker. The computer takes the location of sensor 32 in the X'Y'Z' locating system coordinates as the location of the fiducial marker in this coordinate system. This process is repeated for the other fiducial markers while the head remains immobile. Once this has been completed, input device 130 is actuated to send a further signal indicating that the registration stage is completed. At this time, the computer has locations of all of the fiducial markers in the XYZ tissue image frame of reference, and in the X'Y'Z' locating system frame of reference. Based upon the locations of the fiducial markers in the two frames of reference, the computer calculates an initial transformation between the two frames of reference. Also, when the registration stage is complete, the computer captures initial values for position and orientation of reference sensor 43 in the locating system frame of reference X'Y'Z'.

Once the registration stage is complete, the patients head may be released from the immobilization. The computer tracks position and orientation of the reference sensor 43, and continually compares such position and orientation with the initial position and orientation. The computer continually calculates a new transform between the current position and orientation of the reference sensor and the initial position and orientation of the reference sensor. This transform is combined with the transform between the coordinate systems discussed above to yield an updated transform between coordinate systems. Thus, as the patients head moves, the transform between the locating system coordinate system and the tissue image coordinate system is continually updated.

Figure 3:
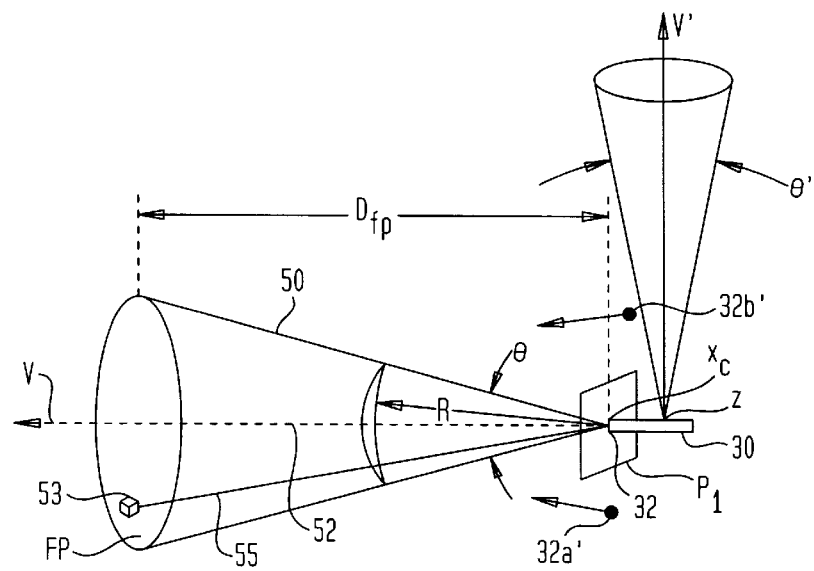
FIG. 3 is a diagrammatic, perspective view of a portion of apparatus in accordance with one embodiment of the present invention.

The physician then inserts the distal end of instrument 20 into the patient's body the location and orientation of the sensor 32 in the X'Y'Z' locating system frame of reference is continually monitored and continually transformed to the XYZ tissue image frame of reference. The transformed location and orientation of the probe corresponds to the position and orientation of the probe in the tissue image frame of reference. The system then generates and displays images corresponding to the image which would be seen from a particular viewpoint point on the instrument, looking in a particular viewing direction from the probe. Stated another way, the viewpoint of the synthetic images has a defined spatial relationship to the instrument. For example, the vector V extending from the tip 32 of the probe along the axis of elongation of instrument 20 represents one such viewpoint and viewing direction. Because the position of tip 32 and the orientation of vector V in tissue image space XYZ are known, the system can generate images corresponding to the image which would be seen through a hypothetical lens positioned at tip 32 and having its central axis pointing in the direction of V. The generated images can have any chosen field-of-view $\theta$ (FIG. 3). Moreover, the generated images can show that portion of the body at any selected distance from the lens. That is, the generated images can be composed from information taken from voxels lying in the field of view at a particular distance from the hypothetical lens or from voxels disposed on a plane, referred to as the "far plane", perpendicular to the central axis V and intersecting the central axis at a particular distance from the hypothetical lens. For example, far plane FP (FIG. 3) passes through axis V at distance $D_{fp}$ and is perpendicular to orientation vector V.

Extending outwardly from the probe is an imaginary cone 50 with its tip placed at the position of tip 32, with the cone's central axis 52 aligned along the probe's orientation vector V. Cone 50 has an internal angle $\theta$ corresponding to the field of view of the hypothetical lens. Given the user-selected specifications of the cone and far plane, the desired synthetic image can then be generated by extracting the data set of those voxels which lie on the plane within the cone. Each point in the image corresponds to a point on the far plane. Each point in the synthetic image is assigned one or more optical values such as brightness, color or both, depending on the tissue characteristic represented by the tissue data recorded in the MR or CT image for the voxel lying at the corresponding point on the far plane. For example, in a CT image, the tissue data for each voxel represents the X-ray density of the tissue within the voxel. In one simple imaging scheme, each point in the synthetic image may be assigned brightness inversely proportional to the X-ray density of the tissue within the voxel disposed at the corresponding point on far plane FP. With this technique, the present invention, in one preferred embodiment, can present on a video monitor the same image that a real endoscope would see if it were placed at the position and orientation of the probe 30, assuming that the anatomical details did not change after the scanning procedure, and assuming that the tissue disposed between the position of the probe and the far plane were transparent. When instrument 20 is moved within the patient, the position and/or orientation of the sensor 32 also changes. Position detecting system 150 detects the new position and/or orientation of the sensor and adjusts the position and orientation of V, cone 50 and far plane FP accordingly. The image displayed by the system thus changes in the same way as a real endoscopic image changes as instrument 20 moves. This greatly facilitates use of the images for guiding the instrument. For example, if the physician is attempting to move the instrument towards a lesion 62 within the patient's body, he or she can align the instrument with the lesion by centering the lesion in the synthetic image. Likewise, the physician can thread the instrument through the venous system, through cavities within the brain or through other cavities or openings, using the synthetic images to align the instrument with the body features in the same manner as he or she would use a conventional endoscopic image.

The physician can use the instrument to affect structures within the body, and thereby perform an interventional procedure. As used in this disclosure, the term "interventional procedure" means a procedure in which a structure within the body is touched or affected by the instrument. For example, where the instrument is a tubular catheter as discussed above, a treating element such as a cauterization or ablation electrode may be advanced into engagement with a lesion or other bodily structure through the lumen after the tip of the instrument has been aligned with the bodily structure using the imaging capabilities. Treatment can also be performed by applying medicament or radiant energy through the lumen of the instrument. The sensor-equipped instrument itself may incorporate treating capability, as where the instrument is an elongated ablation electrode or electrosurgical device. The imaging may continue during the treatment. The ability to maneuver the instrument into position using images which move as if they were seen from the instrument and actually treat the bodily structure has not been available heretofore in instruments other than endoscopes with actual optical elements.

In addition to synthesizing a viewpoint projecting forward from the probe tip along vector V at a given depth and field-of-view, any desired viewpoint can be generated with respect to the known position of the tip of the probe. For instance, a viewpoint could be generated looking directly upward from the tip of instrument 20 and from sensor 32 (i.e., perpendicular to vector V). Viewpoints could also be generated inwardly toward the tip of the probe or even from another arbitrary point at a given distance from the known position of the probe tip. For example, the user may command the system, via input device 130, to present a view taken from an arbitrary viewing location Z at a short distance from the distal end of instrument 20, with a viewing direction V' pointing in an arbitrary direction, and with an arbitrary field of view θ'. The user thus can alter the defined spatial relationship between the viewpoint of the image and the instrument during the interventional procedure. With this capability, the user can "look around" the vicinity of the instrument tip in a way which is impossible with a real endoscope. In a particularly useful arrangement, two images can be presented at two viewpoints 32a' and 32b' offset at known distances and in known directions from the instrument tip, to provide a stereoscopic image wherein the intraocular distance corresponds to the distances between the viewpoints. Where such a stereoscopic image is to be generated, the display device 140 associated with the computer can include a head-mounted display to be worn by the physician, with individual monitors displayed to each eye, or other conventional stereoscopic video devices.

Preferably, the images are generated in real-time and the characteristics of the image can be adjusted by the user in a number of ways. For instance, the surgeon or other medical personal can adjust the field of view (FOV), depth, perspective, focal length and "lens" characteristics (e.g., fish-eye or wide-angle views) of the displayed images. The characteristics of the "lens" may be selected to image points on a sphere of constant radius R from the "lens" rather than on a plane. In the arrangements discussed above, the synthetic image is synthesized from only those voxels disposed in the selected far plane or spherical segment. The tissue lying between the hypothetical lens and the far plane or sphere is not taken into account in generating the synthetic image. Preferably, however a more sophisticated class of image synthesis algorithms, referred to herein as "volume visualization" is employed. As used in this disclosure, the term "volume visualization" refers to an image synthesis system in which actual or assumed optical properties for voxels lying within a specified three-dimensional region in space are employed to generate the image.

One simple volume visualization technique, referred to herein as "ray casting" utilizes a viewing direction, field of view and far plane or spherical shell as discussed above. However, in this technique, the system generates theoretical rays extending from the theoretical lens position or viewpoint to the far plane or spherical shell. The ray extending from the viewpoint to each point in the far plane is associated with the corresponding pixel in the synthetic image. The system sums the assumed opacity of the voxels lying on each ray. Each pixel is assigned a brightness value inversely proportional to the sum of the assumed opacity on the associated ray. In this manner, the synthetic image can include opacity values for the tissues lying between the viewpoint and the far plane or shell. For example, the brightness of the synthetic image at point corresponding to a particular point 53 on far plane FP may include a component representing the contributions to synthetic image of the tissues in the voxel at point 53, as well as a further component representing contributions to the image by other tissues in other voxels along the ray 55 leading from point 53 to the hypothetical lens at viewpoint point 32. The contributions by these other tissues depend on the values for such voxels represented by the tissue images.

Other, more sophisticated volume visualization techniques may be employed. These techniques are generally similar to those used in so-called "virtual reality" systems. Typically, volume visualization systems utilize assumed values of optical properties such as specular and diffuse reflectivity, opacity, and color for the various elements to be depicted. Color may be incorporated in the assumed values of other optical properties, as by providing different assumed value of reflectivity or opacity for light at different wavelengths. A volume visualization system typically also employs an assumed source or sources of illumination, positioned at one or more locations at known positions relative to the objects to be depicted. By known processes, the volume visualization system uses this data to calculate the brightness and color of each pixel in the image. In the method according to this aspect of the invention, the assumed optical properties assigned to the tissue in each voxel are related to the properties of the tissue within that voxel as set forth in the image data. In a simple example, in a monochrome system the assumed reflectivity of the tissue in each voxel may be inversely related to X-ray density for the tissue in such voxel as record in the image data, and the assumed opacity of the tissue in each voxel along the ray may be directly related to X-ray density. In a more complex system, color and other optical properties may be correlated to proton density in MRI imaging information according to a threshold scheme. Thus, voxels with proton density in one range may be assumed to belong to one type of tissue and may be assigned a preselected set of optical properties, whereas voxels with proton density other ranges may be assumed to belong to other tissue types and assigned other preselected sets of optical properties. The optical properties in each such set may be realistic optical properties for the types of tissues involved (e.g., white opaque for bone and red translucent for blood), or else may be arbitrarily selected to enhance visibility. Given the viewpoint, field of view, lens properties and assumed illumination, and the optical properties of the voxels within the field of view, the problem of reconstructing the image reduces to the same problem as that encountered in conventional volume visualization systems, and the same algorithms can be employed.

Moreover, the user can adjust the optical properties for the anatomical surfaces being displayed. For instance, object 60 in FIG. 2 may represent an internal object of interest, such as a tumor, with an outer surface 62 and an inner surface 64. With a conventional endoscope, the surgeon could only see what was directly in front of the endoscope and thus would only see outer surface 62 if an endoscope was positioned outside of the object 60. With the present invention, however, during the surgical procedure, without moving the probe, the user can adjust the weight assigned to data for voxels between the far plane and the hypothetical lens, and thereby adjust the relative transparencies of the outer and inner surfaces 62 and 64 such that outer surface 62 can be displayed as partially transparent to allow viewing inner surface 64 of object 60.

As discussed above, many position locating systems may be employed in systems according to the invention. Preferably, however, the present invention utilizes a system for detecting the position and/or orientation of an object using magnetic or electromagnetic fields. Such systems typically employ field transmitters, such as electromagnet coils 155, disposed at known locations in a fixed reference frame and one or more sensors, such as coils or other transducers, mounted to the object to be located.

In operation, each field transmitter projects a magnetic field varying in space in a fixed frame of reference. The pattern of variation in space for each transmitter is different than the pattern for each other transmitter. The field patterns of the transmitters are displaced or rotated relative to one another and relative to the fixed frame of reference. The sensor or sensors on the instrument then detect the parameters of the field prevailing at the location of the probe as, for example, the magnitude and/or direction of the field at the probe or the magnitudes of individual components of the field at the probe in one or more preselected directions. The transmitters may be actuated in a predetermined sequence so that at any time only one transmitter is active and therefore the field prevailing at the probe is only the field contributed by one transmitter, plus a background field due to the Earth's magnetic field and other environmental sources.

The transmitters can also be driven at different frequencies so that components of the signal from the sensor varying at different frequencies represent contributions to the field at the probe from different transmitters. Based upon the detected parameters of the fields from the individual transmitters, and the known pattern of variation of the field from each transmitter, the computer 100 can then calculate the position and orientation of the sensors, and hence the position of the probe bearing the sensors, in the fixed frame of reference of the transmitters, i.e., in the X'Y'Z' locating system frame of reference.

In a variant of this system, the probe 30 can carry one or more transmitters, whereas a plurality of receiving coils or other transducers are then disposed at various locations and/or orientations in the fixed frame of reference. The location and/or orientation of the probe can then be deduced from signals representing the parameters of the field prevailing at the various fixed transducers. Such systems of this general nature, for example, are disclosed in U.S. Pat. Nos. 4,849,692; 4,642,786; 4,710,708; 4,613,866 and 4,945,305. Other position locating systems can also be used such as systems employing sonic emitters (or detectors) such as piezoelectric crystals located on the instrument and sonic detectors (or emitters) disposed about the fixed frame of reference.

In certain preferred embodiments disclosed in the aforementioned International Patent Publication WO 95/09562, the locating system includes electromagnets which are operable to generate a plurality of different magnetic fields. Each field has at least one component with a non-zero magnitude that is either constant, linear or nearly linear with respect to distance in a particular direction within a sensing volume. Such an arrangement provides less variation in field magnitude throughout the sensing volume than a comparable arrangement in which the field strength varies as the third or higher power of distance. Thus, with the quasi-linear fields, the difference between minimum and maximum field within a given sensing volume is substantially smaller.

Another locating system is disclosed in commonly assigned, copending U.S. patent application Ser. No. 08/476, 380, the disclosure of which is hereby incorporated by reference herein. Certain preferred embodiments of the '380 application provide apparatus for determining position including field generating means for producing a plurality of magnetic fields. The field generating means is arranged to provide such fields having parameters, such as field strength and/or field direction, varying with location within a sensing volume according to known patterns of variation. The pattern of variation for each field is different than the pattern of variation for each other field. For example, where the field generating means includes a plurality of transmitting coils, the coils are disposed at different locations and/or different orientations relative to the sensing volume. Apparatus according to this aspect of the invention of the '380 application also includes at least one sensor adapted to detect one or more parameters of the field prevailing at the sensor when the sensor is at an unknown location within the sensing volume, and to provide one or more sensor signals representing such detected parameters. For example, the sensor may include a sensor body and a plurality of component sensors disposed on the sensor body, each component sensor being operative to measure the magnitude of a magnetic field component in a preselected local direction relative to the sensor body to provide a component sensor signal representing that particular component of the field prevailing at the sensor. The apparatus further includes calculation means for calculating the location of the sensor, the orientation of the sensor or both based upon the sensor signals and upon the unknown patterns of variation of the fields. The apparatus also includes feedback control means for adjusting the field generating means to alter the known pattern of variation of at least one of the fields responsive to the sensor signals, to the calculated location of the sensor or both so as to maintain the detected parameters of the altered field at the sensor within a preselected range. For example, where the field generating means includes a plurality of transmitters disposed adjacent the sensing volume, the feedback control means can be arranged to increase the strength of the field transmitted by a particular transmitter when the sensor is remote from such transmitter, and to decrease the strength of the field emitted by that transmitter when the sensor is close to the transmitter. Thus, the parameters of the field detected at the location of the sensor will always lie within a relatively narrow range of values. Because the transmitted field is altered in a known manner, the position and/or orientation of the sensor can still be calculated, simply by using the altered field as the basis for calculation.

The procedure discussed above with reference to FIGS. 1–3 will now be discussed on a more mathematical basis. Prior to the performance of the interventional procedure, a tissue image data set representing the region of interest of the patient is obtained with respect to the XYZ tissue image frame of reference and stored in data storage device 120. This data set may be obtained by any imaging modality capable of generating data for volumetric regions in the body, as, for example MR (magnetic resonance); CT (computerized tomography), PET (positron emission tomography) or the like. Each data point in the tissue image data set consists of a "tissue value" referenced by virtue of its geometrical placement within a slice within the data set to a three-dimensional spatial coordinate within the XYZ tissue image frame of reference. For instance, in the case of X-ray CT modality, each data point tissue value represents the sampled X-ray absorption or Hounsfield value at its corresponding spatial coordinate. In the case of MR modality, each data point tissue value may represent the sampled relaxation of nuclear spin magnetization value at its corresponding spatial coordinate within the data volume.

Regardless of the specific type of acquisition modality used, the image data set or image volume obtained is then preferably organized in a three-dimensional array containing data representing tissue values whose spatial coordinates are indexed according to a referencing pointer. The image volume is defined with respect to a first XYZ tissue image coordinate system $\Omega_S$, (with S denoting "scanned") and is characterized by the relative position of the scanned anatomy to the scanning device.

A second coordinate system corresponding to the X'Y'Z' patient reference frame, $\Omega_C$, represents the frame of reference of the patient as determined by the locating system, and is related to $\Omega_S$ during the interventional procedure through a transformation T* involving a translation and a rotation. This transform can be expressed as:

$$x_S = A \cdot x_C + T^*, \quad x_c \in \Omega_C, \quad x_S \in \Omega_S.$$

In this equation, $x_S$ represents the coordinate vector of a given point in the tissue image XYZ reference frame at a given location, $x_C$ represents the coordinate vector of the same point in the X'Y'Z' reference frame of the patient, A is a 3×3 orthogonal matrix with three independent real parameters, and T* is a translation vector representing three additional independent parameters.

In a preferred embodiment of the present invention, during the interventional procedure, the $\Omega_C$ to $\Omega_S$ transform T* and matrix A are maintained in real-time as discussed above to allow for patient mobility. Both the position of probe 30 and the positions of the registration sensor 43 are preferably obtained in real-time using one of the preferred position locating systems. The initial rigid body transformation vector and matrix can be calculated from the initial positions of the fiducial markers 40 using a least squares minimization algorithm, such as the well-known Gauss or Levenberg-Marquardt algorithms. That is, during the initial registration stage, the parameters of the transform T* and matrix A are assumed and applied to the coordinate vectors for the registration fiducial markers as determined by the locating system to calculate positions of the fiducial markers in the XYZ coordinate system. The differences between the calculated positions and the known positions of the imaging fiducial markers are determined and a total error function is calculated. These steps are repeated while adjusting the assumed parameters of T* and A until the error function is minimized. Having determined the initial $\Omega_C$ to $\Omega_S$ transform, the transform is updated by monitoring the position and orientation of the reference sensor 43 and calculating a second transform which would transform the current position and orientation of reference sensor 43 in $\Omega_C$ back to the original position and orientation in $\Omega_C$. This transform is then combined in series with the initial transform to provide a combined transform, which can be applied to transform the current position of sensor 32 on the instrument back to the equivalent position in $\Omega_S$. In a simple arrangement, the two transforms can be applied in sequence, so that each new position and orientation of sensor 32 is first transformed back to an equivalent position in $\Omega_C$, compensated for patient movement, and then transformed from that position to a position in $\Omega_S$. Alternatively, the two transforms can be combined and the combined transform can be applied to each new position and orientation of sensor 32.

Given the position of sensor 32 and hence the position of the distal end 21 of instrument 20 in $\Omega_S$ space, the patient image information can be searched and voxel subsets can be isolated that would contribute to an image at a virtual lens position and orientation having any known relationship to the distal end of the instrument, i.e., any known position and orientation relative to sensor 32. As discussed above, in one embodiment the image is generated by considering the viewpoint to be the view from a "virtual" endoscope lens at the location and orientation of the sensor itself. The orientation vector V extends from the sensor 32 and passes through the sensor's major axis corresponding to the axis of elongation of instrument 20. The tip 32 of the instrument can be considered the center of the virtual lens.

Extending outwardly from the focal point is imaginary cone 50 with its vertex placed at the position of instrument tip 32 corresponding to position $x_s$ of the sensor in the XYZ coordinate system in the tissue image frame of reference, i.e., in $\Omega_S$. The cone's central axis 52 aligned along orientation vector V. The cone has an arbitrary included angle θ corresponding to the field of view selected by the user. Once the size and geometry of the cone is selected, the desired synthetic image can then be generated by selecting pixels in $\Omega_s$ space falling within the cone. In an embodiment using a preselected far plane, the computer system then selects those voxels on a far plane FP orthogonal to V at the desired distance from the hypothetical lens center point or vertex $x_S$, and lying within the cone. The computer then transforms the tissue value (e.g., X-ray density in CT image data) of each such voxel into a brightness value, and maps these brightness values into pixels of the image to be displayed. The image is then shown on the display monitor 140.

In another, equivalent approach, the cone encompassing the field of view of the hypothetical lens is specified in the locating system frame of reference. To ascertain the subset of the image information to be display, the spatial coordinates of the vertex of the cone (the hypothetical lens location) in the locating system reference frame are converted to the tissue image reference frame using the equation:

$$x_S = A \cdot x_C + T^*.$$

Next, the orientation vector $V_c$ of the cone in the locating system frame of reference is converted to a vector in the tissue image reference frame using the equation:

$$V_S = A \cdot V_C.$$

Note that the translation vector T* is not used in the above formula since the origin of the orientation vector is implicitly corrected when the location of the vertex or hypothetical lens is transformed.

A cone with defining properties $x_C$, $V_C$, field-of-view (FOV) is thus mapped under transformation to a cone with the scanned defining properties $x_S$, $V_S$, and with the same FOV and maximum depth. In a further variant, the maximum depth of the cone may be defined by a far plane which is disposed at an arbitrarily selected oblique angle to the viewing direction, rather than orthogonal to the viewing direction.

A second subset of interest is a hemispherical sphere $P_1$ (FIG. 3), or any intersection of the hemisphere with a cone of a given field of view, with the center at the tip of the probe. With this shape, the view of the hemisphere shell can be mapped onto a plane to create a disc as the image. The points that are selected from the imaging data and mapped to form the image are the points that belong to the spherical shell and are disposed within the cone representing the given field of view.

The position $x_s$ and orientation vector $V_s$ derived as above can be further translated to yield alternative viewpoints and viewing orientations, such as viewpoint z and vector V'; viewpoints 32a' and 32b' for a stereoscopic image as mentioned above; or any other viewpoint having any specified geometric relationship to the sensor. Stated another way, once the position and orientation of the sensor 32 are specified, the position and orientation of any other element assumed to be rigidly connected to the sensor are also specified. For example, sensor 32 need not be disposed precisely at the distal tip 21 of instrument 20; provided that the region of the instrument between the sensor and the distal tip is short enough that such region can be treated as rigid without serious error, a viewpoint at the tip of the instrument can be generated from the position and orientation of the sensor. The position and orientation of the hypothetical lens derived as described above can also be used in more complex imaging schemes using the volume visualization techniques discussed above.

The images formed are without aberration and are independent of any possible physical obstruction. However, in the embodiments discussed above, the accuracy with which the displayed image represents the image which would be seen through a real endoscope depends upon two implicit assumptions. First, the embodiments discussed above assume that the patients anatomy remains unchanged from the time that the patient is scanned to the time of the interventional procedure using the instrument, and remains unchanged during that procedure. Second, the embodiments discussed above assume that the involved region of the patient moves as a rigid body. For example, it is implicitly assumed that when the patients skull moves, the brain moves with it.

Figure 4:
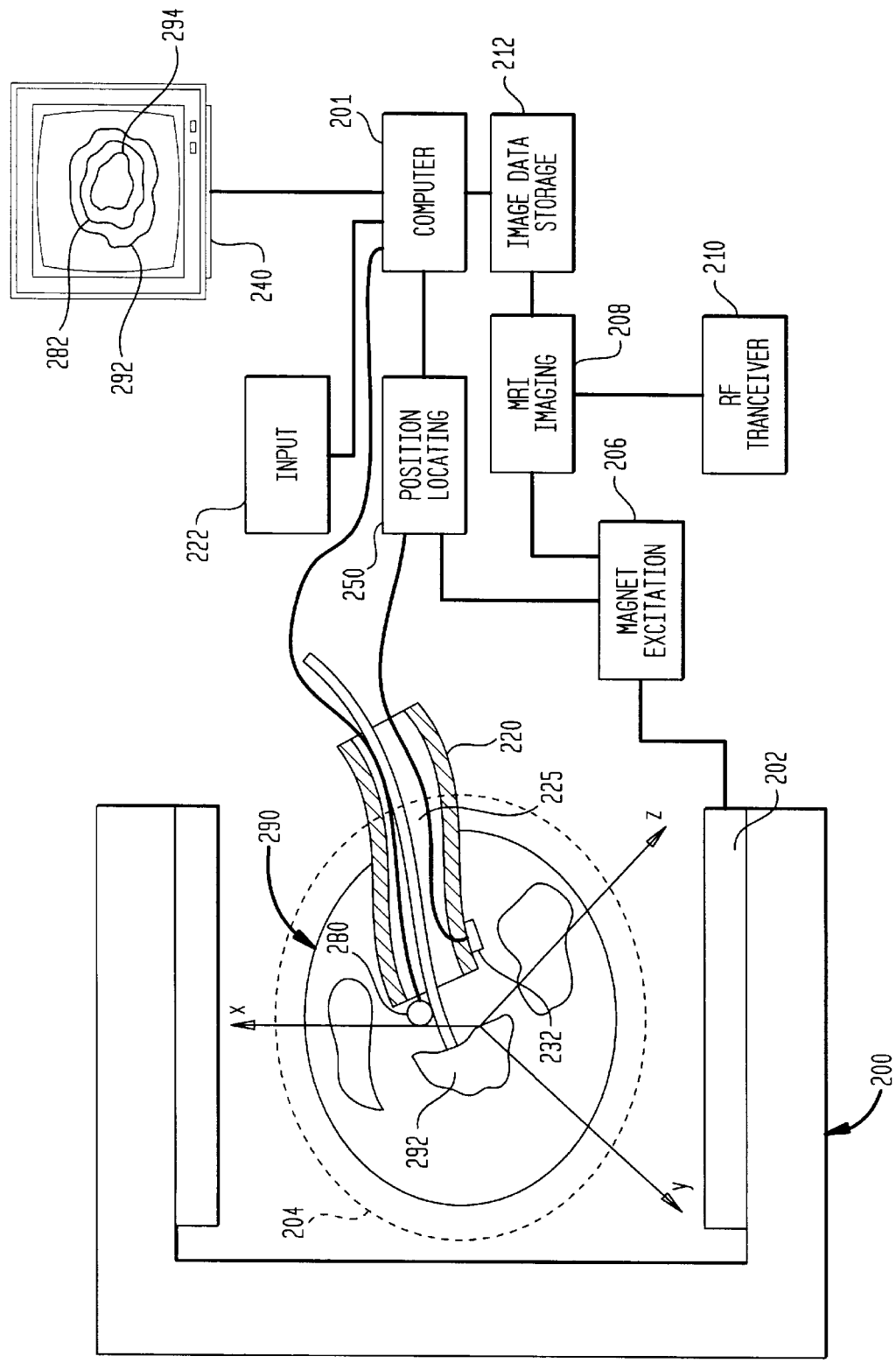
FIG. 4 is a diagrammatic view with certain elements shown in block form, depicting apparatus in accordance with one embodiment of the present invention.

In the embodiment of FIG. 4, the interventional procedure occurs during the imaging step. The apparatus of FIG. 4 includes an instrument 220 such as a catheter having a lumen 225 and a sensor 232 disposed adjacent the tip of the catheter. Sensor 232 is adapted to detect parameters of magnetic fields prevailing at the sensor. Sensor 232 is linked to a position locating system 250 similar to that described above, which in turn is linked to a computer 201 having input device 222 and display 240, all similar to the corresponding components discussed above.

The apparatus further includes a magnet assembly 200 of the type commonly utilized in magnetic resonance imaging. Magnet assembly 200 includes gradient coils 202 adapted to generate linear field gradients in any of several directions within an imaging volume 204 as commanded by magnet excitation unit 206. Magnet assembly 200 is also arranged to maintain a constant or "static" field in imaging volume 204. The field gradients are superimposed on this static field. An MRI imaging control computer 208 and radio frequency transceiver 210 are also provided. These components may be conventional MRI imaging equipment. In known manner, these components are arranged to apply RF excitation to the body of a patient disposed in volume 204 and excite atomic nuclei into resonance, so that the nuclei emit RF resonance signals. By applying the field gradients, the system encodes the resonance signals with spatial information. This process is repeated many times, using different gradients in each repetition. In the conventional manner, the system can construct an image of the internal structures within the patient from the signals obtained in these multiple repetitions, and provides that image to image storage unit 212. This image data includes image values in multiple voxels as discussed above. The image data is referenced to the XYZ coordinate system of the instrument, i.e., to the tissue image reference frame.

Positioning system 250 does not incorporate separate magnetic field transmitters. Instead, the positioning system is linked to magnet excitation unit 206, so that the positioning system can use the magnet assembly 200, including gradient coils 202, to apply magnetic field gradients within volume 204. Locating system 250 derives the location and orientation of sensor 232 by monitoring the magnetic field components detected by sensor 232 during application of gradients by the positioning system. The gradients applied by the positioning system are thus in known spatial relationship with the gradients used in the imaging system. Indeed, the field gradients used by the positioning system may be identical to those used by the MRI imaging system. Therefore, the position derived by imaging system 250 will be in the same frame of reference as the image derived by MRI imaging unit 208. Thus, the position and orientation of sensor 232 will be obtained directly in the tissue image frame of reference XYZ. In operation, the positioning system and MRI imaging system operate simultaneously, while the physician is maneuvering instrument 220 in the body of a patient 290 disposed in volume 204. For example, the positioning system may apply field gradients and acquire position and orientation information during intervals between repetitions of the magnetic resonance imaging process. Alternatively, the gradients applied in the magnetic resonance imaging process may also serve as the gradients used by the locating system. In the manner discussed above, the system uses the position and orientation of the sensor, together with the image data from the MRI system, to derive and display an image 282 (or multiple images) corresponding to that which would be seen from a viewpoint on instrument 220. In this arrangement, both the position and orientation of the sensor and the image data are continually updated during the interventional procedure, and neither of the assumptions discussed above are required.

The instrument of FIG. 4 also has a transducer 280 such as a thermistor for monitoring temperature; an electrode for monitoring cardiac potential; or any other device for measuring a physiologic variable within the patient's body. That transducer is linked by appropriate signal conditioning equipment (not shown) to computer 201. As the tip of instrument 220 traverses a range of positions within the patient's body, computer 201 records values of the physiologic variable associated with each position in the XYZ coordinate system. This information may be displayed as a map or other perceptible indication superposed on the displayed image. For example, as the physician looks at lesion 292 in the patient's body as displayed in image 282, the physician sees contour lines 292 denoting regions having the same temperature.

The present invention overcomes many problems created by the use of traditional endoscopes. Because the probes are substantially smaller than conventional endoscopes, they can be employed in small devices such as small intravascular catheters. The present invention can be used in locations where endoscopes are difficult or potentially dangerous to insert such as the brain. Problems such as chromatic aberration caused by diffraction and refraction and imperfectly focused lens are now eliminated since the present invention is a "camera-less" system. Depth perception problems are eliminated since the user can select any desired depth and field of view. The requirement of a light source is eliminated as well as lighting problems such as unwanted internal reflections. The system can provide very small-diameter instruments with good visualization capability. The instrument or instruments provided with visualization capability may include essentially any instrument to be inserted into the patient. For example, in a surgical procedure, instruments such as scalpels, retractors, cauterization electrodes, guide wires and the like can all be provided with sensors an their positions can be tracked in the same manner as discussed above. Numerous instruments used in the same procedure can be provided with visualization capability.

Substantially the same principles as described with reference to FIG. 4 can be employed with other imaging modalities, such as with CT or even ultrasonic imaging systems. The locating system may include components such as coils mounted in fixed positions relative to a CT or ultrasound system. According to a further embodiment of the invention, the step of determining the position and orientation of the instrument distal end may be performed by the imaging system itself, without a separate position locating system.

The position-sensing elements of the instruments discussed above is referred to herein as a "sensor" inasmuch as the sensing element commonly receives signals sent from antennas disposed outside of a patient's body during use of the instrument. However, the term "sensor" as used herein should also be understood as encompassing one or more elements which can send a signal to external receiving antennas. For example, any of the coil arrangements discussed above can serve either as a receiving antenna array or as a transmitting antenna array. The terms "sensor" should be understood as including transmitting antennas capable of converting signals such as electrical signals into emitted electrical or magnetic fields. These terms should also be understood as referring to elements which can convert electrical signals into light, sonic signals or other signals. For example, certain catheter locating schemes use ultrasonic signals radiated by a transducer in the catheter.

As discussed above, the apparatus and methods according to the present invention can provide synthetic images without the need to acquire actual image information from a viewpoint on the instrument. However, the invention can also be used with instruments having actual imaging capabilities. For example, the instrument used in the present invention can incorporate a conventional endoscope with optical devices such as a lens and fiber optic or electronic system for capturing actual images. Alternatively or additionally, the instrument can include non-optical devices for acquiring actual images such as ultrasonic imaging transducers. The actual images acquired by such devices can be used in conjunction with the synthetic images. For example, the actual image can be superimposed on the synthetic image, or displayed separately. As discussed above, the synthetic image can incorporate information not present in an actual image, as where the actual image is limited by an opaque anatomic feature. Where the actual imaging device provides only a limited field of view, the actual image may be displayed superposed over a larger synthetic image, so that the actual image is seen in a central region whereas the synthetic image is seen in a peripheral region surrounding the central region. This arrangement provides the physician with a "big picture" view including surgical landmarks which would not be visible in the limited scope of the actual image.

Systems other than the fiducial-marker system discussed above can be employed to bring the locating system frame of reference into registration with the tissue image frame of reference. In one known system for registering an instrument locating system to tissue image data, the user traces homologous contours along opposite sides of a symmetrical body part such as the skull using the instrument. The computer generates various alternate transforms between the frames of reference and picks the transform which results in the lowest total error or discrepancy between the homologous contours. In a further known alternative, the user touches the instrument to well-defined landmarks on the body, such as to the bridge of the nose or the joints between bones of the skull, and signals the computer when the instrument is at each landmark. The landmarks thus serve essentially the same function as the fiducial markers discussed above.

As these and other variations and combinations of the features discussed above can be utilized without departing from the present invention as defined by the claims, the foregoing description of the preferred embodiments should be taken by way of illustration rather than by way of limitation of the present invention.

What is claimed is:

1. Medical apparatus comprising:
   (a) a flexible nonimaging instrument having a distal end insertable into a patient's body during an interventional procedure;
   (b) image storage means for storing image information of the patient's body obtained prior to the interventional procedure;
   (c) locating means for determining the position of the distal end of the instrument within the patient's body during the interventional procedure; and
   (d) image generation means for generating synthesized visual images during the interventional procedure from the previously-obtained image information and the determined position of the distal end corresponding to images that would be seen through a virtual lens disposed at a defined spatial relationship to the distal end of the instrument.

2. The apparatus as claimed in claim 1, wherein said locating means further determines the orientation of the instrument distal end within the patient's body and said image generation means generates said synthesized visual images based on said stored image information and the determined position and orientation of said distal end.

3. The apparatus as claimed in claim 2, wherein said instrument has a sensor mounted on the instrument adjacent the distal end thereof, and wherein said locating means includes means for determining the position of the sensor by monitoring one or more parameters of one or more fields transmitted to or from said sensor.

4. The apparatus as claimed in claim 3, wherein said image storage means is operative to store said image information in a tissue image reference frame, said locating means being operative to determine the position and orientation of said sensor in a patient reference frame different than said tissue image reference frame, said image generation means including means for registering the position and orientation of said instrument with the image information in a common reference frame.

5. The apparatus as claimed in claim 4, wherein said means for registering is operative to transform said position and orientation of said sensor as determined by said locating means into a position and orientation in said tissue image reference frame, and wherein said tissue image reference frame comprises said common reference frame.

6. The apparatus as claimed in claim 3, wherein said sensor is adapted to detect magnetic field components in at least two different local directions relative to the sensor, and wherein said locating means includes:
   (i) a plurality of magnetic field generating sources for generating a plurality of different magnetic fields in a sensing volume;
   (ii) control means for actuating said sources to generate said magnetic fields in a predetermined sequence;
   (iii) calculation means for determining the position of said sensor from the magnetic field components detected by said sensor during generation of said magnetic fields.

7. Apparatus as claimed in claim 3, wherein said image storage means includes means for storing data defining an image of the patient in a tissue image reference frame, said locating means includes means for determining the location of the sensor relative to a locating system reference frame, the device further including registration means determining one or more transformations between said frames of reference and a common frame of reference, said image generating means including means for applying said one or more transformations to bring the location of said instrument as determined by said locating means and the tissue image data stored in said storage means into a common frame of reference.

8. The apparatus as claimed in claim 7, wherein said registration means includes imaging fiducial markers attachable to the patient, a reference sensor for attachment to the patient and means for monitoring position and orientation of the reference sensor.

9. The apparatus as claimed in claim 7, wherein said registration means is operative to generate said one or more transformations in real time as the patient moves and said image generating means is operative to apply said one or more transformations in real time to allow for patient movement during an interventional procedure.

10. The apparatus as claimed in claim 3, wherein said locating means includes transmitter means for transmitting signals and said sensor is adapted to sensing said transmitted signals to determine the location of said instrument.

11. The apparatus as claimed in claim 3, wherein said sensor is adapted to transmit signals and said locating means includes means for monitoring said transmitted signals to determine the location of said instrument.

12. The apparatus as claimed in claim 1, further comprising a display monitor for displaying said synthesized visual images.

13. The apparatus as claimed in claim 1, wherein said image generation means includes means for generating said synthesized visual images by volume visualization.

14. Medical apparatus comprising:
(a) a flexible nonimaging instrument insertable into the body of a patient during an interventional procedure;
(b) image storage means for storing image information of the patient's body obtained prior to the interventional procedure;
(c) locating means for determining the position of the instrument within the patient's body during the interventional procedure;
(d) user input means for accepting data specifying an arbitrary location of a viewpoint relative to the instrument and data specifying a viewing direction relative to the instrument; and
(e) image generation means for generating synthesized visual images during the interventional procedure from the previously-obtained image information, determined position of the instrument and said data specifying an arbitrary location and viewing direction, corresponding to images that would be seen through a virtual lens disposed at the viewpoint and viewing direction specified by said data supplied to said input means.

15. The apparatus as claimed in claim 14, wherein said input means is operative to accept data specifying a pair of viewpoints and viewing directions and said image generation means is operative to generate said synthesized visual images in pairs.

16. The apparatus as claimed in claim 14, wherein said input means is operative to accept data specifying field of view for said synthesized visual images.

17. The apparatus as claimed in claim 14, wherein said image generation means includes means for generating said synthesized visual images by volume visualization.

18. Medical apparatus comprising:
(a) a flexible nonimaging instrument insertable into the body of a patient during an interventional procedure;
(b) image storage means for storing image information of the patient's body obtained prior to the interventional procedure;
(c) locating means for determining the position of the instrument within the patient's body during the interventional procedure; and
(d) image generation means for generating synthesized visual images during the interventional procedure from the previously-acquired image information and the determined position of the instrument corresponding to images that would be seen through a virtual lens disposed at a defined spatial relationship to said instrument by volume visualization.

19. The apparatus as claimed in claim 18, further comprising user input means for accepting data specifying said defined spatial relationship.

20. The apparatus as claimed in claim 17 or claim 18 or claim 13, wherein said image generation means includes means allowing user selection of an assumed position of an illuminating source.

21. The apparatus as claimed in claim 17 or claim 18 or claim 13, wherein said image generation means includes property adjustment means allowing user selection of one or more assumed optical properties of tissues.

22. The apparatus as claimed in claim 21, wherein said property adjustment means is operative to allow selection of assumed opacity of tissues.

23. The apparatus as claimed in claim 21, wherein said property adjustment means is operative to allow selection of assumed reflectivities of tissues.

24. The apparatus as claimed in claim 21, wherein said property adjustment means is operative to allow user selection of assumed colors of tissues.

25. The apparatus of claim 1 or claim 14 or claim 18, wherein said instrument includes a transducer mounted on the instrument for measuring at least one physiologic variable and value display means for incorporating visually perceptible representations of one or more values of said physiologic variable on said synthesized visual image.

26. The apparatus as claimed in claim 25, wherein said value display means includes mapping means for displaying a plurality of values of said physiologic variable measured at a plurality of positions of said instrument as a map of said variable versus position in said synthesized visual image.

27. The apparatus as claimed in claim 1, wherein said instrument is less than 3 mm in diameter.

28. The apparatus as claimed in claim 1 or claim 14 or claim 18, wherein said image storage means is operative to store data obtained from magnetic resonance imaging of the patient.

29. The apparatus as claimed in claim 28, wherein said locating means is includes a magnet system of an magnetic resonance imaging system and means for measuring one or more characteristics of a magnetic field prevailing at the instrument.

30. A method of providing images during an interventional procedure comprising the steps of:
(a) inserting a distal end of a flexible nonimaging instrument into a patient's body during the interventional procedure;
(b) providing tissue image information defining an image of the patient's body obtained prior to the interventional procedure;
(c) determining the position of the distal end of the instrument within the patient's body during the interventional procedure; and
(d) synthesizing visual images of the patient's body during the interventional procedure from the previously-acquired image information and the determined position of the distal end of the instrument corresponding to images that would be seen through a virtual lens disposed at a defined spatial relationship to the distal end of the instrument.

31. The method as claimed in claim 30, further including the step of determining the orientation of said instrument within the patient's body, wherein said step of synthesizing further includes synthesizing said visual images based on said image information and said determined position and orientation of said instrument.

32. The method as claimed in claim 31, wherein said instrument has a sensor mounted thereon adjacent said distal end, and wherein said step of determining position and orientation includes the step of transmitting one or more fields to or from the sensor determining one or more parameters of the transmitted fields, and deriving the position and orientation of said sensor from said one or more parameters.

33. The method as claimed in claim 32, wherein said step of providing said image information includes the step of providing the image information in a tissue image reference frame, and said step of determining the position of said instrument is performed so as to determine the position and orientation of said in a locating system reference frame different than said tissue image reference frame, said step of synthesizing including the step of registering the position and orientation of said instrument with the image information in a common reference frame.

34. The method as claimed in claim 33, wherein said step of registering includes the step of transforming said position and orientation determined by said step of determining the position of said instrument into a position and orientation in said tissue image reference frame, whereby said tissue image reference frame is said common reference frame.

35. A method of providing images during an interventional procedure comprising the steps of:
(a) inserting a flexible nonimaging instrument into a patient's body during the interventional procedure;
(b) providing tissue image information obtained prior to the interventional procedure defining images of the patient's body;
(c) determining the position and orientation of the instrument within the patient's body during the interventional procedures;
(d) during said interventional procedure, accepting user-supplied data defining a spatial relationship between the viewpoint and the instrument; and
(e) synthesizing visual images of the patient's body during the interventional procedure from the previously-obtained tissue image information, the determined position and orientation of the instrument and said user-supplied data, corresponding to images that would be seen through a virtual lens disposed at said spatial relationship to the instrument defined by said user-supplied data.

36. The method as claimed in claim 35, wherein said user-supplied data specifies the field of view and viewing direction of said synthesized visual images.

37. A method as claimed in claim 36, wherein said step of synthesizing said visual images is performed by volume visualization.

38. A method of providing images during an interventional procedure comprising the steps of:
(a) inserting a flexible nonimaging instrument into a patient's body during the interventional procedure;
(b) providing tissue image information obtained prior to the interventional procedure defining images of the patient's body;
(c) determining the position and orientation of the instrument within the patient's body during the interventional procedure; and
(d) synthesizing visual images of the patient's body during the interventional procedure from the previously-acquired tissue image information and the determined position and orientation of the instrument corresponding to images that would be seen through a virtual lens disposed at a defined spatial relation to the instrument by volume visualization.

39. The method as claimed in claim 30 or claim 36 or claim 38, further comprising the step of displaying said synthesized visual images on a display monitor.

40. The method as claimed in claim 30, wherein said step of synthesizing said visual images is performed by volume visualization.

41. The method as claimed in claim 35 or claim 38 or claim 40, further comprising the step of adjusting the characteristics of said synthesized visual images.

42. The method as claimed in claim 41, wherein said adjusting step includes the step of selecting an assumed position or positions of one or more illuminating sources.

43. The method as claimed in claim 41, wherein said adjusting step includes the step of selecting one or more assumed optical properties of tissues.

44. The method as claimed in claim 43, wherein said one or more assumed optical properties include assumed opacities of tissues.

45. The method as claimed in claim 43, wherein said one or more assumed optical properties include assumed reflectivities of tissues.

46. The method as claimed in claim 43, wherein said one or more assumed optical properties include assumed colors of tissues.

47. The method as claimed in claim 30 or claim 35 or claim 38, wherein said step of providing tissue image information includes the step of obtaining said tissue image information by magnetic resonance imaging of the patient.

48. The method as claimed in claim 47, wherein said magnetic resonance imaging step is performed using an MRI imaging magnet assembly and wherein said step of determining position and orientation of the instrument includes the step of determining one or more parameters of the magnetic fields provided by said MRI imaging magnet assembly and deriving the position and orientation of said sensor from said one or more parameters.

49. The method as claimed in claim 30 or claim 35 or claim 38, further comprising the step of treating the patient through said instrument.

50. Medical apparatus comprising:
(a) a flexible nonimaging instrument insertable into a patient's body during an interventional procedure;
(b) an image storage device storing image information of the patients body obtained prior to the interventional procedure;
(c) a position locating system operative to determine the position of the instrument within the patient's body during the interventional procedure; and
(d) a computer including a program operative to generate synthesized visual images during the interventional procedure from the previously-obtained image information and the determined position of the instrument corresponding to images that would be seen through a virtual lens disposed at a defined spatial relationship to said instrument.

* * * * *

UNITED STATES PATENT AND TRADEMARK OFFICE
CERTIFICATE OF CORRECTION

PATENT NO. : 6,016,439
DATED : January 18, 2000
INVENTOR(S) : Acker

It is certified that error appears in the above-identified patent and that said Letters Patent is hereby corrected as shown below:

Abstract, line 1, "view point" should read --viewpoint--.
Column 3, line 49, under column entitled "Summary of the Invention", "a" should read --an--.

Column 5, line 12, "including" should read --includes--.
Column 5, line 30, "a" should read --an--.
Column 5, line 32, "a" should read --an--.
Column 5, line 44, "includes" should read --include--.
Column 6, line 14, "assembly" should read --assembly.--
Column 6, line 54, "includes an instrument 20" should read --includes an instrument 20.--.
Column 8, line 7, after "panel display" insert the word --is--.
Column 8, line 20, delete the word "of".
Column 8, line 61, "patients" should read --patient's--.
Column 9, line 15, "X'Y'Z'" should read --"X'Y'Z'.--.
Column 9, line 26, "patients" should read --patient's--.
Column 9, line 31, "patient's body the" should read --patient's body. The--.
Column 12, line 27, after "density" insert the word --in--.
Column 15, line 66, after "52" insert the word --is--.
Column 17, line 10, "patients" should read --patient's--.
Column 17, line 16, "patients" should read --patient's--.
Column 18, line 43, "lens" should read --lenses--.
Column 18, line 55, "an" should read --and--.

UNITED STATES PATENT AND TRADEMARK OFFICE
CERTIFICATE OF CORRECTION

PATENT NO. : 6,016,439
DATED : January 18, 2000
INVENTOR(S) : Acker

It is certified that error appears in the above-identified patent and that said Letters Patent is hereby corrected as shown below:

Column 22, line 49, delete the word "is".
Column 22, line 49, "an" should read --a--.
Column 23, line 23 after "said" insert the word --instrument--.
Column 24, line 11, "36" should read --35--.
Column 24, line 54, "patients" should read --patient's--.

Signed and Sealed this

Twenty-seventh Day of February, 2001

Attest:

NICHOLAS P. GODICI

Attesting Officer    Acting Director of the United States Patent and Trademark Office